(12) United States Patent
Miljkovic

(10) Patent No.: US 6,251,420 B1
(45) Date of Patent: Jun. 26, 2001

(54) ISOFLAVANOID FORMULATIONS FOR ORAL ADMINISTRATION

(76) Inventor: Dusan Miljkovic, 4787 Cather Ave., San Diego, CA (US) 92122

( * ) Notice: Subject to any disclaimer, the term of this patent is extended or adjusted under 35 U.S.C. 154(b) by 0 days.

(21) Appl. No.: 09/600,944
(22) PCT Filed: Jan. 27, 1999
(86) PCT No.: PCT/US99/01771
§ 371 Date: Jul. 24, 2000
§ 102(e) Date: Jul. 24, 2000
(87) PCT Pub. No.: WO99/38509
PCT Pub. Date: Aug. 5, 1999

Related U.S. Application Data

(60) Provisional application No. 60/072,914, filed on Jan. 28, 1998.

(51) Int. Cl.[7] .......................... A61K 47/00; A01N 43/30
(52) U.S. Cl. .............................. 424/439; 514/456
(58) Field of Search ........................ 424/439; 514/456; 549/290

(56) References Cited

U.S. PATENT DOCUMENTS 5,085,682 * 2/1992 Safir et al. ........................... 71/88

* cited by examiner

*Primary Examiner*—Jose' G. Dees
*Assistant Examiner*—Alton Pryor
(74) *Attorney, Agent, or Firm*—Fish & Associates, LLP; Robert D. Fish

(57) ABSTRACT

Preparation of a nutritional supplement, comprising: providing a mixture containing an isoflavanoid and a solvent; removing a sugar portion from the isoflavanoid to produce an isoflavanoid aglycone; concentrating the aglycone to at least 10 wt % in the mixture; and coupling the aglycone with an amphiphilic carrier to produce micelles having an average diameter of less than about 1000 nm.

19 Claims, 1 Drawing Sheet

ISOFLAVANOID FORMULATIONS FOR ORAL ADMINISTRATION

This application claims the benefit of provisional application filed 60/072,914 filed Jan. 28, 1998. This application is a 371 of PCT/US 99/01771 filed Jan. 21, 1999.

FIELD OF THE INVENTION

The field of the invention is nutritional supplements.

BACKGROUND OF THE INVENTION

Isoflavanoids comprise a large class of compounds, many of which have significant biological effects. Certain isoflavanoids belong to a broader class of phytoestrogens, compounds found in the plant kingdom that possess chemical structure and biological activity similar to estrogens. (see Merck Index, XII Edition, No. 4395).

Estrogens and phytoestrogens have overlapping, but not coextensive, effects on different tissues in the body. For example, estrogens have a much more pronounced effect on breast and uterine tissue than phytoestrogens, but both estrogens and phytoestrogens have strong salutory effects on blood vessels and bone. Although the mechanisms are not yet completely elucidated, the divergence has recently been explained as a function of the differing activities of these compounds upon different classes of estrogen receptors. Estrogens are reported to have a pronounced effect on both estrogen receptor alpha (ERα) predominantly expressed in breast and uterine tissue, and on estrogen receptor beta (ERβ) which is predominantly expressed in endothelial cells of blood vessels, and osteoclasts and osteoblasts of bone. In contrast, phytoestrogens have only a relatively small effect on ERα, but a relatively great effect on ERβ. (Kuiper, G. G. M. J., Enmark, E., Pelto-Huikko, M., Nilsson, S., and Gustafsson, J-A., "Cloning of a novel estrogen receptor expressed in rat prostate and ovary", *Proc. Natl. Acad. Sci. USA* 93, 5925–5930, 1996; Mosselman, S., Polman, J., and Dijkema, R., "ERβ:Identification and characterization of a novel human estrogen receptor", *FEBS Lett.* 392, 49–53, 1996; Jan-Ake Gustafsson: "Estrogen receptor beta—Getting in on the action", *Nature Medicine*, 3 (number 5), 493–494 (May 1997), and Iafrati, M. D., Karas, R. H., Aronovitz, M., Kim S., Sullivan, Jr., T. R., Lubahn, D. B., O'Donnell, T. F., Korach, K. S., and Mendelsohn M. E., "Estrogen inhibits the vascular injury response in estrogen receptor alpha-deficient mice", *Nature Medicine*, 3, (number 5), 545–548 (1997)).

Taken together, these findings explain many of the seemingly contradictory biological activities of estrogens and phytoestrogens. For example, since breast and ovarian tissue contains mostly ERα receptors, estrogens (as in estrogen replacement therapy) increases the risk of breast and ovarian cancer, while phytoestrogens do not. (Kuiper, G. G., Carlsson B., Grandien, K., Enmark, E., Haggblad, J., Nilsson, S., and Gustafsson J-A. "Comparison of the ligand binding specificity and transcript tissue distribution of estrogen receptors alpha and beta", *Endocrinology*, 138(3), 863–870 (1997)). Similarly, since bone deposition is controlled in part by ERβ, both estrogens and phytoestrogens can increase bone density. (see, for example, Migliaccio, S., Davis V. L., Gibson, M. K., Gray, T. K., and Korach, K. S., "Estrogens modulate the responsiveness of osteoblast-like cells (ROS 17/2.8) stably transfected with estrogen receptor", *Endocrinology*, 130(5), 2617–2624 (1992); and Davis, V. L., Couse, J. F., Gray, T. K., and Korach, K. S., "Correlation between low level of estrogen receptors and estrogen responsiveness in two rat osteoblast-like cell lines", *J Bone Miner Res* 9(7), 983–991 (1994)).

In view of these findings, long-term nutritional supplementation with isoflavanoids, and in particular with phytoestrogens, has great potential. Moreover, while such supplementation has an especially important effect in women, the fact that ERβ is also present in male endothelial cells, osteoblasts and osteoclasts, leads to the conclusion that such compounds can also be useful in protecting men as well against arteriosclerosis and osteoporosis.

Among the more active phytoestrogens are genistin and genistein (see FIG. 1). These compounds are found in low concentration in soybeans, red clover, and several other plants, and ingestion of products made from these sources has indeed been associated with reduced incidence of circulatory and skeletal disease. Genistein and some other accompanying natural isoflavanoids (such as biochanin A) have also demonstrated chemopreventive activity in a variety of cancers (see, for example: Messina et al., *Nutrition and Cancer*, 21, 113–131, 1994; and Barnes, S., Sfakianos, J., Coward, L., and Kirk, M., in *Dietary Phytochemicals in Cancer Prevention and Treatment*, American Institute for Cancer Research, Plenum Press, New York, 1996, p87–100). Genistein and soybean isoflavanoids are especially effective in inhibition of cancer cell growth in breast (Pagliacci et all., *Eur J Cancer* 30A, 1675–1682, 1994) prostate (Peterson and Barnes, *Prostate*, 22, 335–345, 1993) and colon (Kuo, *Cancer Letters*, 110, 41–48, 1996). In addition, some genistein derivatives show pronounced curative properties in some type of cancer, apparently through growth inhibition of cancer cells (see, for example, the publication of Uckun et al, *Science*, 267, 886–891, 1995), describing genistein immunoconjugates that are highly efficient in treating B-cell precursor (BCP)-leukemia, a common form of childhood cancer). The mechanisms by which genistein and other related isoflavanoid compounds exhibit anti-cancer activity are believed to include tyrosine kinase(s) activity, topoisomerase II inhibition, antioxidant activity (free radical scavenging), angiogenesis inhibition, apoptosis induction and cell differentiation induction (see review by Peterson, J Nutr 125, 784S–789S, 1995).

Industrial mixtures of crude isoflavanoid are currently produced either as a side product of soybean processing, or by extraction of selected medicinal plants (like red clover). Contemporary nutritional supplement industry practice usually starts with such crude isoflavanoid mixtures, and then merely powders and compresses the mixtures into tablet and capsule forms. Alternatively, isoflavanoids are sometimes concentrated along with the protein components of soybeans into the well-known soybean based foods and drinks such as tofu, miso, and so forth.

The isoflavanoid content in such products is almost always low, typically ranging from between 0.02% and 1%. Only rarely is the isoflavanoid content in nutritional supplements increased, and then only to about 40% A great majority of these higher quality products are based on genistin or other isotlavanoid glucosides. Pure isoflavanoid is extremely expensive.

In addition to relatively low concentration of isoflavanoids, nutritional supplements and soybean based foods typically contain isoflavanoids in a form that has very poor bioavailability. The situation is exacerbated by the fact that genistein and its 7-O-glucoside, genistin, are readily biotransformed in hepato-biliary circulation to 7O-glucuronide and/or to the corresponding 7O-sulfate, which is excreted through the urine. As a result, isoflavanoid blood levels in humans are in sub-micromolar region, even with high intake of isoflavanoids. (see, for example, Barnes, S. et al. cited above).

Without being limited by the validity of any particular theory or practice, it is contemplated that genistein or analogous isoflavanoids must usually reach a blood concentration of between 1–10 micromoles/liter to achieve a desirable biological activity (such as maintaining the bones healthy, with a satisfactory bone density, keeping the blood vessels free from cholesterol plaques, or for the purpose of cancer chemoprevention, etc.) (Barnes, S. et al., cited above). Due to various combinations of low concentration and poor bioavailability of the active isoflavanoids in the supplements, the desired blood concentrations cannot realistically be achieved over the short term by administering any of the existing market preparations. Thus, there is a strong current need for an isoflavanoid preparation having improved concentration and bioavailability, and particularly for preparations providing improved concentration and bioavailability of genistein, genistein, and/or derivatives thereof.

Recently, the pharmaceutical industry introduced microemulsification technology to improve bioavailability of some lipophilic (water insoluble) pharmaceutical agents. Examples include Trimetrine (Dordunoo, S. K., et al., *Drug Development and Industrial Pharmacy*, 17(12), 1685–1713, 1991 and REV 5901 (Sheen, P. C., et al., *J Pharm Sci* 80(7), 712–714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

Interestingly, it appears that microemulsion formulations have never been used in the field of nutritional supplements. The likely reasons are that (1) microemulsion formulations are rather expensive relative to the price that can be charged for the end product, and (2) the number of GRAS (Generally Recognized As Safe) emulsifiers/co-emulsifiers and solvents/co-solvents that can be employed to implement microemulsification in the nutritional field is considerably smaller the corresponding number in the pharmaceutical field. An additional difficulty in the field of isoflavanoids is that relatively expensive concentration and purification steps are generally required to achieve proper microemulsification.

In short, there is a strong, ongoing need to provide relatively concentrated, and highly bioavailable formulations of isoflavanoids, especially of genistein, genistin, and derivatives thereof:

SUMMARY OF THE INVENTION

The present invention provides formulations of nutritional supplements that contain an isoflavanoid aglycone coupled with an amphiphilic carrier, and methods of producing the same.

In one aspect of preferred embodiments, the formulations contain micelles formed from the isoflavanoid aglycone and amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm. In another aspects of preferred embodiments, the formulations are manufactured from an extract of a natural isoflavanoid source, preferably soybean or red clover. The isoflavanoids employed are preferably genistein or a genistein derivative, and have phytoestrogen activity.

Preferred methods involved concentrating the aglycone to at least 20 wt % in a mixture, with more preferred methods concentrating the aglycone to at least 30 wt %, 40 wt % or even 50 wt % in the mixture. Such concentration may be carried out simultaneously with a mild enzyme or acid hydrolysis in a "one pot" procedure.

Oral supplements according to the invention may provide between 50 mg and 100 mg or more of the isoflavanoid aglycone, and such supplements may be dosed to produce a serum concentration of the isoflavanoid aglycone of at least 1 $\mu$M.

DETAILED DESCRIPTION OF PREFERRED EMBODIMENTS

Isoflavanoid supplements can be formulated in a way that greatly increases the bioavailability of the isoflavanoid, while cost-effectively providing relatively high concentrations. In general, contemplated methods involve several modifications to the naturally occurring form of isoflavanoid, including: hydrolyzing or in any other manner removing the sugar portion of the isoflavanoid to produce an isoflavanoid aglycone; concentrating the aglycone to at least 10 wt % in the mixture; and micro/nano-emulsifying the aglycone by coupling the aglycone with an appropriate amphiphilic carrier to produce micelles having an average diameter of less than about 100 nm. These modifications can be undertaken sequentially, or preferable simultaneously in a "one-pot" procedure.

In principle, almost any isoflavanoid containing composition may be employed as a starting material. At the moment, the only cost-effective compositions are extracts from isoflavanoid containing plants, and in particular extracts from soybean and red clover. Soybean extract, commonly known as soybean molasses, are especially desirable because they are typically produced as a byproduct of soybean processing, and are therefore relatively inexpensive. In the future it is contemplated that isoflavanoids may also be readily available from other sources, including from biosynthetic sources, such as may be provided through genetic engineering. This latter route is contemplated to be particularly advantageous because the bacteria or other biosynthetic sources may be engineered to provide the aglycosidic isoflavanoids.

Figure 1:
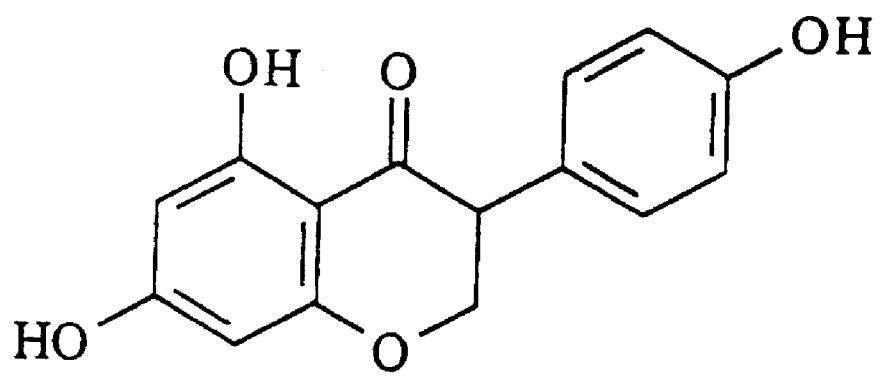
FIG. 1 is prior art chemical structure representation of genistein.
Figure 2:
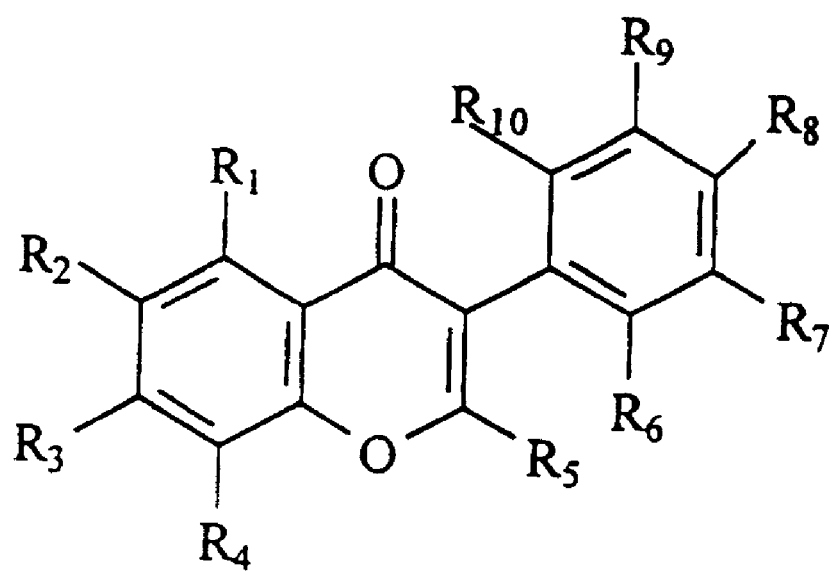
FIG. 2 is a chemical structure representation of contemplated genistein derivatives.

Because of the considerable body of evidence relating to nutritional and medical uses of genistein, it is especially contemplated that methods and formulations contemplated herein may employ genistein as an isoflavanoid. It is, however, contemplated that other isoflavanoids may be employed instead of, or in addition to genistein, including any of the various genistein derivatives satisfying the structure of FIG. 2.

Regardless of their source, or the particular isoflavanoid being employed, glycosidic forms of isoflavanoids are not generally suitable for micro/nano-emulsion formulation because the glycosides tend to be insoluble in a majority of available emulsifier/solvent systems. It was discovered, however, that upon acid hydrolysis to the corresponding aglycone form, isoflavanoids do indeed generally become suitable for micro/nano-emulsification. By way of illustration, genistin (7-O-genistein-glucoside) may be acid hydrolyzed to genistein (its corresponding aglucone), and that modification allows genistein to be efficiently microemulsified.

The hydrolysis can be accomplished in many different ways, and all suitable methods are contemplated herein. Having experimented with many such methods, the most suitable process identified to date involves boiling the glycosides in ethanol over several hours. with a catalytic amount of concentrated aqueous HCl. A particularly purified aglucone product is obtained when acid hydrolysis is carried out in the presence of cellite, silica and/or active carbon. Some insoluble proteinaceous and carbohydrate residues that are otherwise difficult to filter off are readily removed by subsequent filtration.

The ethanol soluble aglucone is readily dissolved in any suitable emulsifier/co-emulsifier and solvent/co-solvent system. Particularly suitable emulsifiers/co-emulsifiers contemplated herein include polyethylene glycol derivatives such as polyethylene glycol mono-oleate, polyethylene glycol di-oleate, and polyethylene glycol mono- and di-laurate. Other suitable choices are polyglycerol fatty acid esters and ethoxylated sorbitan and sorbitol fatty acid esters. Less polar co-emulsifiers, such as propylene glycol mono-laurate can also be used for preparation of isoflavanoid micro/nano-emulsified formulas. Other surface-active ingredients (preferably having GRAS status) can also be used, including lecithin and other naturally occurring emulsifiers.

While any convenient solvent may be used, preferred solvents are relatively non-toxic, such as ethanol, acetone and water, and the polyethylene glycols, including glycols of various molecular weights. Other suitable solvents are glycerol, polyglycerol, ethyl and diethyl ether of diethylene glycol.

It was quite unexpectedly discovered that concentration, purification and hydrolysis of isoflavanoids can be carried out simultaneously in a "one-pot" procedure. In an exemplary procedure, the starting material is a powdered, relatively concentrated source of soybean isoflavanoids. Freeze dried soybean molasses may be used, and typically contains between about 0.5 to 5% of isoflavanoids, depending of the processing technology used. Ethanol is added to the starting material as a solvent, along with a catalytic amount of concentrated aq. HCl. A cellite/active carbon adsorbent mixture or silica/active carbon adsorbent mixture is also included in a quantity dependent of the purity of the staring material (usually in the range of 40–160% based on the amount of starting material). The reaction temperature can vary from room temperature to 80° C. (reflux temperature), and reaction time varies from about 2–4 hours. Isolation of purified and concentrated aglucones proceeds simply by filtration and evaporation of the filtrate. If desired, further purification can proceed by a filtration of ethanol-hexane solution of concentrated isoflavanoids through a layer of silica. This process produces an aglucone concentrate suitable for further formulation in a micro/nano-emulsion amphiphilic carrier system.

While all suitable amphiphilic carriers are contemplated, the presently preferred carriers are generally those that have GRAS status, and that can both solubilize isoflavanoids and microemulsify them at a later stage when the isoflavanoid solution comes into a contact with a complex water phase (such as one found in human gastro-intestinal tract). Usually, amphiphilic ingredients that satisfy these requirements have HLB (hydrophilic to lipophilic balance) values of 2–20, and their structures contain straight chain aliphatic radicals in the range of $C_6$ to $C_{20}$. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-. di- and mono-fatty acid glycerides and di- and mono-polyethyleneglycol esters of the corresponding fatty acids, with a particularly preferred fatty acid composition including capric acid 4–10, capric acid 3–9, lauric acid 40–50, myristic acid 14–24, palmitic acid 4–14 and stearic acid 5–15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

In many of the experiments performed to date, the final solutions appeared to the naked eye to be completely transparent, and did not appear to separate out over the short term, of at least several hours. Without being limited by the validity of any particular theory or practice, it is contemplated that these results derive from a large percentage of the isoflavanoids being bound in micelles having a diameter smaller than about 1 micron ($\mu$). Many of the particles are thought to be less than 1000 nm in diameter, with other particles being less than about 100 nm in diameter, others less than about 50 nm, and still others being less than about 20 nm in diameter. Most likely, being amphiphilic, the lipid molecular carriers interact with the isoflavanoids via both hydrophobic-hydrophobic and hydrophilic-hydrophilic attractive forces. It is further contemplated that the hydrophilic (surface) parts of the mixed micelles, or lipid nano-droplets, also interact (through attractive forces) with neighboring water molecules, keeping the micelles highly dispersed in the aqueous medium.

The micro/nano-emulsified formulations of isoflavanoid aglycones are expected to have two to four times better bioavailability after their oral administration than other isoflavanoid formulations presently available in the industry. Among other things, it is contemplated that the amphiphilic carriers will at least partially protect the isoflavanoids from being biotransformed in the gut or in the intestinal wall. It is also contemplated that the isoflavanoid-amphiphilic carrier complexes, in addition of being absorbed through the small intestinal wall, will be absorbed through the lymphatic system, and thereby avoid destruction in the hepatic biliary circulation.

EXAMPLE 1

Preparation of isoflavanoid aglucone concentrate from soybean freeze-dried molasses:
Introductory Remarks:

In soybean processing, and in particular in the process of soybean protein purification, industrial plants may accumulate rather large amounts of a valuable side product called soybean molasses. It is usually a dark colored aqueous-ethanol solution of some soybean constituents consisting of saponins, sterols, carbohydrates, odorous materials, organic pigments and isoflavanoid glucosides, just to mention some classes of organic compounds among the other present organic compounds.

There is no a standard soybean molasses. Its content depends on the type of soybean processed, on the particular crop, and on the industrial procedure by which the side product was produced. The work described herein was carried out with soybean molasses obtained from different soybean processing plants, mainly obtained by the inventor from several soybean processing plants out of the United States, and with a majority of the soybean molasses samples imported from "SojaProtein" located in Becej, former Yugoslavia. In most cases, the samples of soybean molasses were freeze-dried, i.e., in powdered form.

The isoflavanoid content was determined in a usual way, using HPLC and comparison with commercially available standards of chemically pure isoflavanoid glucosides or corresponding aglucones. On average, the samples contained 0.5–2% of total isoflavanoids, mainly (more than 95%) in their glucosidic form. Genistin was the main constituent (approximately 70% of the total isoflavanoids, daidzin was present up to 20% and glycetin up to 10% of the total isoflavanoids).

A Typical "One-pot" Experiment:

A sample of freeze-dried soybean molasses (100 g; 2% isoflavanoid content), cellite (20 g), activated carbon (5 g), rectified ethanol (96%, 1L), and conc. HCl (20 ml) were placed in a two liter round bottomed flask fitted with a reflux condenser. The reaction mixture was constantly magnetically stirred and heated at the reflux temperature for 4 hours.

After cooling down to room temperature, the reaction mixture was filtered through Buchner funnel through a cellite layer. Filtration proceeds smoothly. Filtrate has a yellow to light brown color. Upon evaporation of the filtrate using a rotary evaporator in vacuum, one obtains 15–20 g of powdered light brownish material with isoflavanoid content of 10–12%.

Taking this residue in ethanol-hexane (1:1; 100 ml), filtering the soluble (supernatant) part through silica for column chromatography (20 g) and washing the silica with additional 50 ml of ethanol-hexane 1:1, afforded 6–7 g of grayish solid with an isoflavanoid content of 25%.

By repeated ethanol-hexane extraction and filtration through silica, one obtains up to 30%, at least 40, at least 50%, or at least 60% isoflavanoid aglucone concentrate, which is particularly suitable for further formulations, but that can be used without substantial additional modification for nutritional and other purposes.

EXAMPLE 2

Preparation of isoflavanoid aglucone concentrates in amphiphilic media—Formulated micro/nano-emulsifiable isoflavanoid concentrates The isoflavanoid aglucone concentrates, obtained as described in the example 1 (with a 50% total isoflavanoid content), were used for their further formulation.

As a rule 20 weight parts of 50% isoflavanoid concentrate was mixed with 80 weight parts of a mixture of selected amphiphilic carriers and selected solvents. In this way the final formulation would provide 10% of isoflavanoids based on total formulation weight.

In all cases, formulation ingredients (isoflavanoid concentrate, amphiphilic carrier(s) and solvent(s) were mixed at once at room temperature and then the temperature was adjusted to 100° C. to 120° C. and the mixture was heated at that temperature for 5–10 minutes while magnetically stirred. During that time one obtains a clear solution which stays clear when cooled to room temperature. These relatively viscous liquids are pale brown and clear and they flow freely at room temperature (a feature that is important for the intended subsequent encapsulation process—i.e., in manufacturing of soft gelatin capsules).

If for any reason, in rare instances, the final formulation remains turbid at RT, one can centrifuge the same (at 1000 rpm) and use subsequently the supernatant.

Bellow are given the exact compositions of three suitable micro/nano-emulsifiable isoflavanoid formulation:

| Formula A | |
|---|---|
| Purified Isoflavanoid Aglycone Concentrate-50% (PIAC-50) | 20 w.p. |
| Polyethylene glycol-av. MW-400 (PEG-400) | 30 w.p. |
| Polyethylene glycol mono-oleate, MW860 (PEG-MO-860) | 46.5 w.p. |
| Liquid Lecithin (LL) | 3.5 w.p. |
| Formula B | |
| PIAC-50 | 20 w.p. |
| PEG-400 | 25 w.p. |
| PEG-MO-860 | 42.5 w.p. |
| Lauroglycol (LG) | 10 w.p. |
| LL | 2.5 w.p. |
| Formula C | |
| PIAC-50 | 20 w.p. |
| PEG-MO-860 | 40 w.p. |
| PrS20/PS80* | 40 w.p. |

*Protasorb O-20 NF/Polysorbate 80, the product of Protameen Chemicals Inc.

Thus, novel methods and formulations for producing isoflavanoid aglycone nutritional supplements have been disclosed. It should be apparent, however, to those skilled in the art that many more modifications besides those already described are possible without departing from the inventive concepts herein.

What is claimed is:

1. A method of preparing a nutritional supplement, comprising:

providing a mixture containing an isoflavanoid and a solvent;

removing a sugar portion from the isoflavanoid to produce an isoflavanoid aglycone;

concentrating the aglycone to at least 10 wt % in the mixture; and coupling the aglycone with an amphiphilic carrier to produce micelles having an average diameter of less than about 1000 nm.

2. The method of claim 1 wherein the mixture comprises a soybean extract.

3. The method of claim 1 wherein the mixture comprises a red clover extract.

4. The method of claim 1 wherein the isoflavanoid aglycone is genistein.

5. The method of claim 1 wherein the isoflavanoid is genistin.

6. The method of claim 1 wherein the isoflavanoid has the structure:

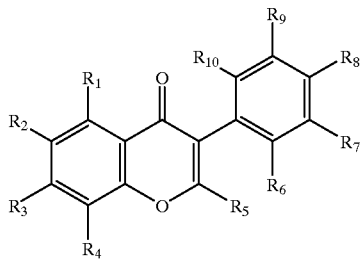

where $R_1$, $R_2$, $R_3$, $R_4$, $R_5$, $R_6$, $R_7$, $R_8$, $R_9$ and $R_{10}$ are independently any monovalent substituent.

7. The method of claim 1 further comprising concentrating the aglycone to at least 20 wt % in the mixture.

8. The method of claim 1 further comprising concentrating the aglycone to at least 30 wt % in the mixture.

9. The method of claim 1 further comprising concentrating the aglycone to at least 40 wt % in the mixture.

10. The method of claim 1 further comprising concentrating the aglycone to at least 50 wt % in the mixture.

11. The method of claim 1 wherein the amphiphilic carrier comprises a glyceride.

12. The method of claim 1 wherein the amphiphilic carrier comprises an at least partially fatty acid.

13. The method of claim 1 wherein the solvent comprises polyethyleneglycol.

14. The method of claim 1 further comprising coupling the aglycone with an amphiphilic carrier to produce micelles having an average diameter of less than about 100 nm.

15. The method of claim 1 further comprising coupling the aglycone with an amphiphilic carrier to produce micelles having an average diameter of less than about 50 nm.

16. A method of supplementing a diet comprising preparing an oral supplement including the micelles according to claim 1 in sufficient quantity to provide at least 50 mg of the isoflavanoid aglycone.

17. A method of supplementing a diet comprising preparing an oral supplement including the micelles according to claim 1 in sufficient quantity to provide at least 100 mg of the isoflavanoid aglycone.

18. A method of supplementing a diet of a consumer comprising:

preparing an oral supplement including the micelles according to claim 1; and the consumer taking the supplement in sufficient dosage to produce a serum concentration of the isoflavanoid aglycone of at least 1 $\mu$M.

19. A method of supplementing a diet of a consumer comprising:

preparing an oral supplement including the micelles according to claim 1; and the consumer taking the supplement in sufficient dosage to produce a serum concentration of the isoflavanoid aglycone of at least 1.5 $\mu$M.

\* \* \* \* \*